United States Patent [19]

Benedict et al.

[11] Patent Number: 5,015,677

[45] Date of Patent: May 14, 1991

[54] ADHESIVES DERIVED FROM BIOADHESIVE POLYPHENOLIC PROTEINS

[75] Inventors: Christine V. Benedict, Farmington; Paul T. Picciano, Canton, both of Conn.

[73] Assignee: Bio-Polymers, Inc., Plainville, Conn.

[21] Appl. No.: 213,439

[22] Filed: Jun. 27, 1988

Related U.S. Application Data

[63] Continuation-in-part of Ser. No. 34,078, Apr. 2, 1987, abandoned, which is a continuation-in-part of Ser. No. 856,597, Apr. 25, 1986, abandoned.

[51] Int. Cl.$^5$ .................. C08H 1/00; C07K 13/00; C12P 21/06
[52] U.S. Cl. ........................ 524/17; 524/21; 524/22; 524/25; 530/328; 530/350; 106/125; 106/133; 106/149; 106/150; 106/157; 106/158; 156/336
[58] Field of Search ............... 524/17, 21, 22, 25; 530/328, 350; 106/124, 125, 126, 127, 128, 129, 130, 133, 138, 139, 140, , 141, 149, 150, 157, 158; 156/326, 336

[56] References Cited

U.S. PATENT DOCUMENTS

| | | | |
|---|---|---|---|
| 2,014,167 | 9/1933 | Bowen | 527/205 |
| 2,164,269 | 6/1939 | Fawthrop | 106/125 |
| 2,246,405 | 6/1941 | Hubbard | 427/384 |
| 2,334,098 | 11/1943 | Hubbard | 427/394 |
| 2,514,789 | 7/1950 | Orth | 527/205 |
| 2,708,169 | 5/1955 | Keil | 106/125 |
| 2,958,605 | 11/1960 | Leiner | 106/125 |
| 3,242,028 | 3/1966 | Hart | 156/336 |
| 3,336,246 | 8/1967 | Golick | 527/205 |
| 3,365,320 | 1/1968 | Minelli | 524/21 |
| 3,438,374 | 4/1969 | Falb et al. | 106/133 |
| 3,444,109 | 5/1969 | Golick | 527/205 |
| 3,563,228 | 2/1971 | Seiderman | 623/66 |
| 3,878,135 | 4/1975 | Keegan et al. | 523/120 |
| 3,891,580 | 6/1975 | Morris et al. | 106/125 |
| 3,926,870 | 12/1975 | Keegan et al. | 523/120 |
| 4,046,955 | 9/1977 | Bye | 428/479 |
| 4,355,137 | 10/1982 | Winter | 525/54.1 |
| 4,362,567 | 12/1982 | Schwarz et al. | 106/157 |
| 4,393,080 | 7/1983 | Pawelchak et al. | 428/355 |
| 4,414,976 | 11/1983 | Schwarz et al. | 106/124 |
| 4,427,808 | 1/1984 | Stol | 524/24 |
| 4,440,884 | 4/1984 | Jannusch | 524/25 |
| 4,496,397 | 1/1985 | Waite | 106/161 |

(List continued on next page.)

OTHER PUBLICATIONS

Waite, *Jour of Biol. Chem.*, "Evidence for a Repeating 3,4-Dihydroxyphenyalalanine and Hydroxyproline-containing Decapeptide in the Adhesive Protein of the Mussel, *Mytilis edulis* L.", vol. 258, No. 5, Mar. 10, 1983, pp. 2911-2915.

(List continued on next page.)

*Primary Examiner*—Nathan M. Nutter
*Attorney, Agent, or Firm*—Kramer, Brufsky & Cifelli

[57] ABSTRACT

An adhesive or coating formulation useful in biomedical application and particularly well suited for use in aqueous environments is provided comprising:

(1) a bioadhesive polyphenolic protein component having from about 5 to about 99 weight percent of a proteinaceous substance comprising from about 10 to about 400 of the following repeating decapeptide unit:

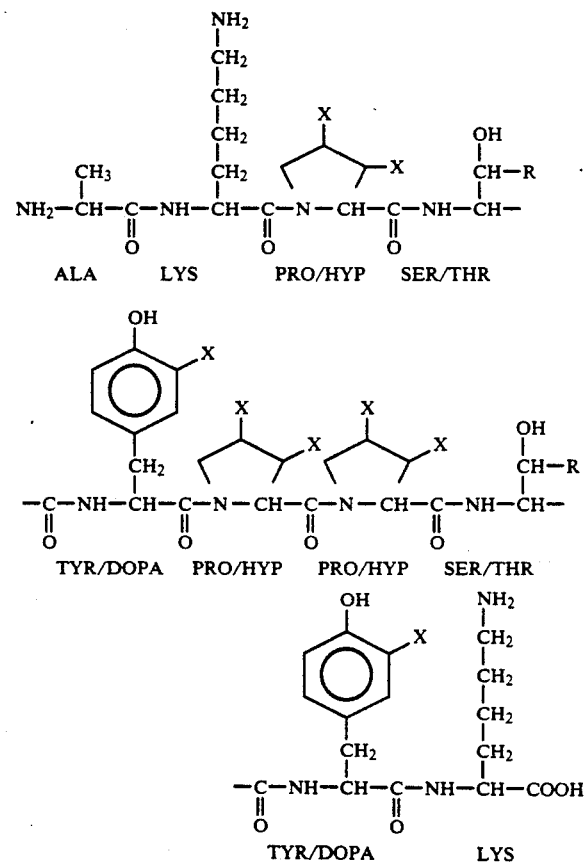

in which each X is hydrogen or hydroxyl and each R is hydrogen or methyl;

(2) from about 1.0 to about 40 weight percent of a cross-linking agent which promotes cross-linking of the decapeptide;

(3) one or more additives which promote the desired properties of the formulation, said additives comprising at least one surfactant and being present in an amount of from 0% to about 90% by weight, and (4) a filler compatible with the intended use of the formulation, said filler being present in an amount of from 0% to about 50% by weight.

34 Claims, No Drawings

U.S. PATENT DOCUMENTS

| | | | |
|---|---|---|---|
| 4,522,753 | 6/1985 | Yannas et al. | 530/356 |
| 4,563,490 | 1/1986 | Stol et al. | 524/24 |
| 4,585,585 | 4/1986 | Waite | 435/69 |

OTHER PUBLICATIONS

"Nature's Underwater Adhesive Specialist", *Int. J. Adhesion and Adhesives*, vol. 7, No. 1, 9–14 (Jan., 1987).

"Novel Materials from Protein–Polymer Grafts", *Nature*, vol. 325, 328–329 (Jan. 22, 1987).

"Mussel Glue from *Mytilus Californianus* Conrad: A Comparative Study", *Journal of Comparative Physiology B*, vol. 156, 491–496 (1986).

"Assay of Dihydroxyphenlalanine (dopa) in Invertebrate Structural Proteins", *Methods in Enzymology*, vol. 107, 397–413 (1984).

"Catechol Oxidase in the Byssus of the Common Mussel, *Mytilus Edulis L.*", *J. Mar. bid. ass. U.K.*, V. 65, 359–371 (1985).

"Polyphenolic Substance of *Mytilus Edulis*: Novel Adhesive Containing L-Dopa and Hydroxyproline", *Science*, vol. 212, 1038–1040 (May 29, 1981).

"Peptide Repeats in a Mussel Glue Protein: Theme and Variations", *Biochemistry, vol. 24, 5010 (1985)*.

"Location and Analysis of Byssal Structural Proteins of *Mytilus edulis*", *Journal of Morphology*, vol. 189, pp. 171–181 (1986).

"Composition and Ultrastructure of the Byssus of *Mytilus edulis*", *Journal of Morphology*, vol. 189, pp. 261–270 (1986).

Bowen, *Dental Adhesive Materials Symposium*, 3d Workshop, pp. 82–95 (1973).

Devore and Gruebel, *Biochem. Biophys. Res. Comm.*, 80: 993–999 (1978).

Devore et al., *J. Dent. Res.*, 58:243 (1979).

Gross and Hoffman, "Medical And Biological Adhesives", In: Skeist, I. (ed.), *Handbook of Adhesives*, 2d ed., Van Nostrand Reinhold Company, New York, pp. 818–835 (1977).

Lindner and Dooley, *Chem. Abstr.*, 87:200 (1977).

Lindner and Dooley, Rept. San Francisco Bay Naval Shipyard, Vallejo, Calif., Paint Lab. Rep. No. 69-3 4D856070 (1969).

Marfuggi, *Univ. of Conn. Health Center Quarterly* 1: 2–6 (1984).

Sherwood et al., Annual Report prepared for the National Institute Dental Research, Report No. NIH-NIDR-70-2237 (1987).

Waite and Gossling, *Ortho. Trans.*, 7:342 (1983).

Waite and Tanzer, *Biochem. Biophys. Res. Comm.*, 96:1554–1561 (1980).

Waite and Tanzer, Cross-linking of Macromolecules, In: Florini, J. (ed.), *Handbook on the Biochemistry of Aging*, CRC Press, Boca Raton, Fla. (1982).

Waite and Wang, *Analytical Biochem.*, 70:279–280 (1979).

Wake, *Adhesion and the Formulation of Adhesives*, 2d ed., Applied Science Publishers, Chapter 13, London and New York (1982).

ADHESIVES DERIVED FROM BIOADHESIVE POLYPHENOLIC PROTEINS

CROSS REFERENCE

This application is a continuation-in-part of copending application Ser. No. 034,078 filed Apr. 2, 1987, which is a continuation-in-part of application 856,597 filed Apr. 25, 1986, now abandoned.

BACKGROUND OF THE INVENTION

This invention relates to adhesive formulations derived from bioadhesive polyphenolic proteins which are useful in biomedical applications and which are particularly well suited for use in aqueous environments. Bioadhesive polyphenolic proteins, originally derived from several species of the mussel genus Mytilus, can be derived either from natural sources or be manufactured synthetically, and contain one or more sequences of repeating decapeptides having the formula:

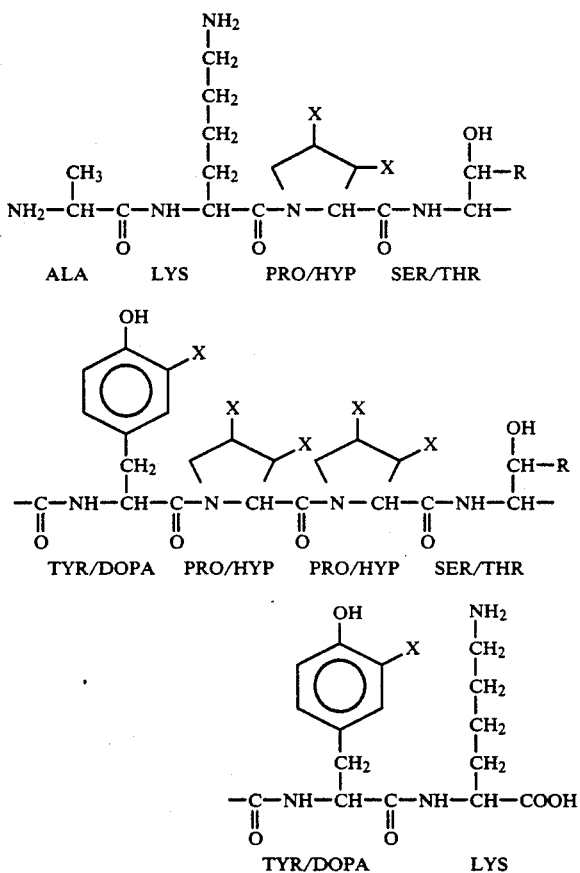

wherein each X is independently selected from the group comprising hydroxyl and hydrogen; and wherein each R is independently selected from the group comprising hydrogen and methyl. As used in this application, the term "bioadhesive polyphenolic proteins" is to be understood as referring to mixtures of proteins containing from about 10 to about 400, preferably from about 50 to about 150, units of the above repeating decapeptides, and optionally may contain other proteinaceous units, and chain extenders. Molecular weight is a key property of these adhesives. As shown in the examples, the unpolymerized decapeptide oligomer is not suitable for use, per se, as an adhesive because sufficient curing cannot be effected to form strong bonds. Ultimately, the adhesive, after curing, exhibits an adhesive strength of at least about 100 gm/cm$^2$ when used on soft tissue, preferably at least about 150 gm/cm$^2$, which indicates that a sufficient amount of intermolecular bonds and bonding between the substrate and the adhesive has been achieved to adhere the substrate to the adhesive.

Naturally-occurring protein from which the bioadhesive polyphenolic protein may be derived is produced and stored in the exocrine phenol gland of the mussel and is deposited onto marine surfaces by the mussel's foot during the formation of new adhesive plaques. Decapeptides may be obtained from the bioadhesive polyphenolic proteins by the method described by Waite in *Journal of Biological Chemistry* 258, 2911-15 (1983), and in U.S. Pat. No. 4,585,585. Additionally, the bioadhesive polyphenolic proteins may be obtained by genetic engineering techniques, well known to those skilled in the art.

Bioadhesive polyphenolic proteins exhibit excellent adhesive properties on a variety of surfaces, particularly surfaces submerged in water. The repeating decapeptides of the bioadhesive polyphenolic protein, are in essence the building blocks for a potentially wide variety of adhesive and coating substances.

The decapeptides and the bioadhesive polyphenolic proteins containing them show great promise for the development of commercial products. Virtually all prior art adhesives perform optimally when first applied on clean, dry surfaces. However, even those adhesives which display water resistant characteristics after curing, for example, resorcinolformaldehyde polymers, fail if applied in excessively moist environments. Bioadhesive polyphenolic proteins and their constituent decapeptides, on the other hand, have the potential to impart water-compatible characteristics to any adhesive formulation through their increased monomeric molecular weight, reduced tendency to diffuse from the application site, and increased number and variety of reactive residues, such as the "phenol-like" residues tryosine and dopa, that are especially capable of displacing water.

However, to date no compositions containing bioadhesive polyphenolic proteins have been available for scientific, medical or commercial use.

Accordingly, it is a principal object of this invention to provide compositions derived from bioadhesive polyphenolic proteins for use in various applications involving the need for adhesion in at least a partially aqueous environment, which applications specifically include, but are not limited to, medicine and surgery, botany, dentistry, underwater applications, chromatography, and the like.

SUMMARY OF THE INVENTION

The adhesive formulations of this invention comprise by weight: (1) from about 5% to about 99% of bioadhesive polyphenolic proteins which contain repeating decapeptides having the formula:

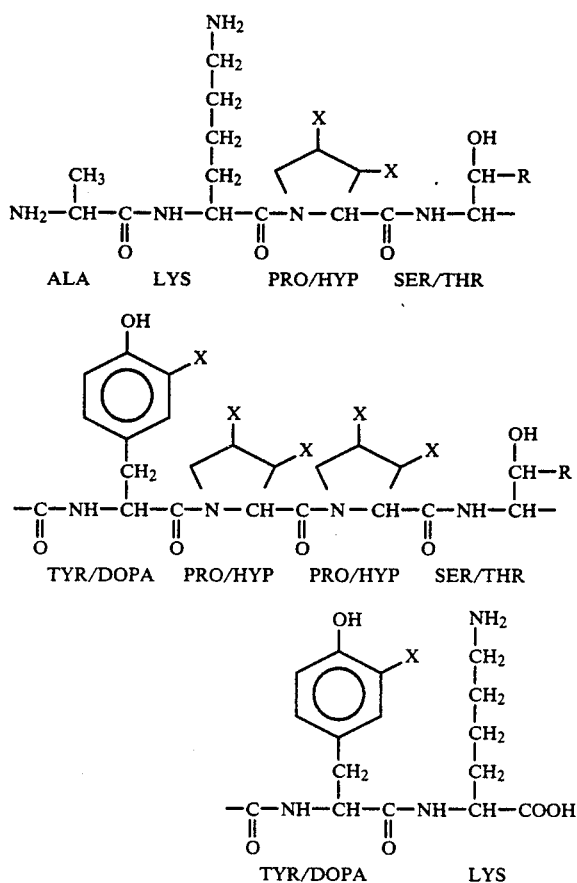

wherein each X is independently hydrogen or hydroxyl, and wherein each R is independently hydrogen or methyl; (2) from about 1.0% to about 40% of a cross-linking agent to promote at least partial cross-linking of the bioadhesive polyphenolic proteins; (3) from about 0% to about 90% of one or more additives for providing desired properties in the completed adhesive/coating formulation; and (4) from about 0 to about 50% of one or more filling agents compatible with the substrate to which the composition is to be adhered.

DETAILED DISCLOSURE

Adhesive formulations of this invention comprise bioadhesive polyphenolic proteins which contain repeating decapeptides, cross-linking agents which promote at least partial cross-linking of the bioadhesive polyphenolic proteins, optionally, one or more additives for providing desired properties in the completed adhesive formulation, and optionally, one or more filling agents compatible with the substrate to which the composition is to be adhered. For the purposes of this description, it should be understood that adhesive formulations may be used to bind two substrates together (a true adhesive application) and in applications wherein the adhesive formulation is applied as a thin film on a substrate (a coating application). In this coating application, bioadhesive polyphenolic protein formulations are useful, for example, in marine environments to prevent the fouling of certain substrates coated with a film of the formulation when submerged for long periods of time under sea or fresh water.

Bioadhesive polyphenolic proteins consist in large part of the above-depicted repeating decapeptide sequence, present from about 10 to about 400, preferably about 50 to about 150, times. If the bioadhesive polyphenolic protein comprises mixtures containing significant amounts of proteins containing less than about 10 repeating decapeptide units, the bioadhesive polyphenolic protein will not attain a sufficient molecular weight upon curing to produce strong bonds and, accordingly, will not adhere the two substrates together On the other hand, if the bioadhesive polyphenolic protein comprises mixtures containing significant amounts of proteins containing more than about 400 repeating decapeptide units, the bioadhesive polyphenolic protein will be too viscous for practical application. Preferably, the bioadhesive polyphenolic protein comprises mixtures containing about 50 to about 150 repeating units so as to maximize the adhesive strength of the protein while still maintaining sufficient fluidity for easy handling.

Bioadhesive polyphenolic proteins thus comprise repeating decapeptide sequences of varying lengths and may also comprise other proteins and chain linking groups such as amino acids, oligopeptides, and various other bifunctional spacers. Amino acids comprise any of the well-known naturally-occurring L-amino acids, as well as other amino acids such as ornithine, homocysteine, citrulline, 3-aminotyrosine, and the like. Oligopeptides include the various di-, tri, tetra-, or penta-peptides and higher peptides which can be readily synthesized or are commercially available. Examples include (ALA-CYS-ALA), (ALA-LYS)$_3$, (ALA-LYS-PRO)$_4$, (PRO-HYP-GLY)$_5$ and the like. Bifunctional spacers include such diverse substances as aliphatic or aromatic dialdehydes, imido esters, isocyanates, aryl and alkyl dihalides, dimaleimides, and the like. Bifunctional spacers also include all the chemical mediators of peptide bond formations, anhydrides, active esters, condensing agents (dicyclohexylcarbodiimide) used in solid and liquid phase peptide synthesis.

The concentration of bioadhesive polyphenolic proteins in the adhesive compositions may vary from about 5% by weight to about 99% by weight, the exact concentration selected depending upon the intended use of the composition.

The second component of the adhesive composition is a cross-linking agent which may be used to promote partial or full cross-linking of the bioadhesive polyphenolic proteins between substrates and the proteins and/or between the additives in the formulation and the proteins. The nature of the cross-linking is uncertain, but is believed to involve covalent bonds, ionic bonds, hydrogen bonds, and Van der Waals bonds, or a combination of these bonds. Here again, the amount of cross-linking agent utilized will depend upon the ultimate use of the adhesive formulation and can vary in amount ranging from about 1.0% to about 40% by weight (5,000 to 50,000 Units/mg adhesive proteins by activity) or more based on the number of repeating decapeptide sequences in the bioadhesive polyphenolic proteins. Generally, the cross-linking agent is utilized in an amount ranging from about 5% to about 20 % by weight and preferably about 8,000 to 20,000 units/mg adhesive proteins by activity. For coating applications, the incubation period is increased and the amount of cross-linking agent can be reduced to less than 1 %. The precise weight percent of cross-linker used, of course, depends upon the molecular weight of the bioadhesive polyphenolic protein and the purity of the cross-linking agent. Suitable cross-linking agents include, for example, enzymatic oxidizing agents such as catechol oxidase, mushroom tyrosinase, or chemical cross-linking agents with any number of reactive functional groups, such agents including glutaraldehyde, formaldehyde, Bis(sulfosuccinimidyl) suberate and 3,3'-Dithiobis (sulfosuccinimidylpropionate) or even chemical oxidizing agents such as oxygen or a peroxide.

The third component of the adhesive formulation is one or more additives which may be used to promote the desired properties in the adhesive composition. For almost all applications, a cationic, anionic or non-ionic surfactant additive may be used, the choice of which depends on the intended use of the particular formulation, and which selection is well within the knowledge of persons skilled in the art. Examples of such surfactants are sodium dodecylsulfate, a sulfate-rich compound, protein or mucoprotein, and sodium dodecylbenzenesulfonate. Other additives may be used, depending on the desired use of the composition. For example, if the adhesive formulation is intended to be conductive for use with two electrically conductive substrates, conductive additives such as a metal salt, for example, silver chloride, silver nitrate, ferric chloride, cuprous sulfate, cupric sulfate, or organometallic coordination compounds such as ferrocene or the like may be used. These additives may comprise up to about 90% by weight of the adhesive composition.

The fourth component of the adhesive composition is one or more fillers, the nature of which depends primarily on the composition and surface characteristics of the substrate to be bonded or sealed. For example, in biomedical applications, the filling agent can be a substance having biocompatible properties such as collagen, albumin, hyaluronic acid, hydroxyapatite, chondroitan sulfate, elastin, laminin, casein, chitin, chitosan, or similar substances. Alternatively (or in addition to the foregoing filling agent), the filling agent may be an inert material similar in nature to one or both of the substrates being joined, as, for example, silica beads for glass, ceramic, or cement substrates, wood or cellulosic fibers or other polysaccharides for woody or non-woody plant tissue, and synthetic polyesters, polyurethanes, polyamines, polyacetates, and the like for industrial (metallic or non-metallic) substrates. The percentage of filler utilized may be up to about 50% by weight of the final adhesive composition.

While specific amounts of the various components can vary greatly depending on the specific intended use of the adhesive or coating composition, the substrate intended to be adhered or coated, bond strength desired, environmental conditions, etc., some general guidelines can be provided for the various broad areas of use.

For water impervious applications, either as adhesive or as coating, the total amount of bioadhesive polyphenolic protein and cross-linking agent preferably ranges from about 25 to about 90 weight percent of the composition. When the composition is to be used in an underwater environment, the bioadhesive polyphenolic protein and the cross-linking agent more preferably total from about 50 to about 80 weight percent of the composition and there is in addition, a surfactant functioning as a spreading agent in an amount of from about 20 to almost 40 weight percent.

For biomedical uses, the additives and fillers should, of course, be biomedically compatible with the organs to which the composition is to be applied. For many uses such as orthopedic repair, reconstruction or prosthetics, the total amount of bioadhesive polyphenolic protein component and cross-linking agent can range from about 30 to about 100 weight percent of the composition.

In adhesive formulations for joining electrically conductive substrates, electrically conductive additives can be present in amounts ranging from about 10 to 80 weight percent.

The following is a partial listing of specific uses for the adhesive and coating compositions of the invention The various useful formulations are merely exemplary of the broad ranges possible for each component of the subject compositions:

(1) An adhesive which may be applied to materials under water (including fresh and salt water) or in a mixed aqueous-organic liquid environment, or to materials prior to their submergence in these environments. A useful formulation is 94% (w/w) bioadhesive polyphenolic protein, with 25,000 Units/mg protein mushroom tyrosinase and 6% (w/w) collagen slurry. In this and other compositions mentioned herein, the units for enzyme activity are as listed by the manufacturer and vary from lot to lot in terms of units per milligram enzyme protein. Therefore, when the cross-linking agent in a formulation is enzymatic, the designation "Unit per milligram" of adhesive formulation protein will be used, rather than weight percent. Another useful formulation includes 94% (w/w) organically synthesized peptide with the sequence [ala-lys-pro-ser-tyr-hypro-hypro-thr-thr-lys]repeated 10 times, 6% collagen and 25,000 Units/mg mushroom tyrosinase.

(2) A biomedical adhesive which may be used in orthopedic repair such as bone to bone repair, bone to tendon repair, bone to ligament repair, tendon to tendon repair, tendon to ligament repair, ligament to meniscus repair, meniscus repair, ligament to muscle repair, muscle repair, and any of the above to alloplastic materials for reconstruction, wound repair, or prosthetic use. An example of such formulation is 65% (w/w) bioadhesive polyphenolic protein; 35% (w/w) collagen slurry as a filler; 6,000 Units/mg protein mushroom tyrosinase cross-linker. Another useful formulation is 58% (w/w) bioadhesive polyphenolic protein with 28,000 Units/mg protein mushroom tyrosinase cross-linker and 42% (w/w) collagen slurry as a filler.

(3) An ophthalmic adhesive which can be used to heal perforations, lacerations or incisions, whether surgically induced or trauma related, in or on the surface of the eye by acting as a tissue filler or which would facilitate the attachment of donor tissue or alloplastic materials over or in the wound. A useful formulation is 83% (w/w) bioadhesive polyphenolic protein with 18,000 Units/mg protein mushroom tyrosinase and 17% (w/w) collagen slurry. Another useful and preferred formulation is bioadhesive polyphenolic protein with 12,000 Units/mg protein mushroom tyrosinase.

(4)(a) An ophthalmic adhesive which may be used to reattach the retina to the back of the eye by direct application of the adhesive to the retina and underlying structure and/or through the direct modification of the vitreous humor or space occupied by the vitreous humor that overlies the retina, and/or by the attachment of alloplastic materials to the external surface of the eye (e.g., for scleral buckles) to modify posterior chamber dimensions and shape to influence retinal repair, or in the repair of retinal breaks resulting from traumatic or nontraumatic injury. A useful formulation for this is described in (3) above. For retinal reattachment, a spot welding application method can be used with pressure applied to the bond by increasing the volume of the vitreous humor with addition of hyaluronic acid.

(4)(b) An ophthalmic adhesive which may be used for the repair or attachment of lenses (synthetic or natural) to adjacent tissues for implantation, for repair of the lens capsule or the interior portions of the lens, and the attachment of other structures to internal or external aspects of the eye needed for repair or reconstruction, such as alloplastic materials, tissues, epi-scleral muscle, contact lenses, and the like. A useful formulation is as described in (3) above.

(4)(c) An ophthalmic adhesive which may be used for the repair, construction, reconstruction, and/or attachment of corneal component parts (epithelium, endothelium, fibroblasts, collagen stroma). A useful formulation is as described in (3) above.

(5) A dental adhesive which may be applied to hold retainers, bridges or crowns in place, to secure loose teeth, or repair broken teeth or hold filler material for caries in place to prevent further tooth decay, or as a prophylactic coating on teeth or on the site of excavated caries to prevent tooth decay. A useful formulation is 50% (w/w) bioadhesive polyphenolic protein with 18,000 Units/mg protein mushroom tyrosinase, 20% w/w collagen slurry and 30% w/w hydroxyapatite.

(6) A medical adhesive which may be used for attachment of tissue or alloplastic grafts to soft tissues for wound repair or as a prosthesis and to promote wound closure in soft tissues such as liver, spleen, stomach, esophagus, intestine, brain, skin, lung, and similar anatomic structures and their subcomponents following disease and traumatic or nontraumatic injury. The adhesive can also be used in conjunction with surgical closure methods for wounds and incisions such as to assist in sealing the holes in tissues created by sutures tacks, staples and/or the suture line being closed. This adhesive is especially useful in situations wherein fluid seepage occurs, i.e., the gastrointestinal tract, the cardiovascular system, the eye, brain, spinal column and the like. A specific formulation for intestine is 74% (w/w) bioadhesive polyphenolic protein with 18,000 Units/mg protein mushroom tyrosinase and 26% (w/w) collagen slurry as filler.

(7) A veterinary adhesive which may be used in the repair of split hooves and similar collagenous tissue, cartilagenous tissue, or some other connective tissue, bone tissue and/or soft tissue wounds in animals. A useful formulation is as described in (6) above.

(8) An anti-fouling, nonbiodegradable, nontoxicant-releasing coating that may be applied under water or prior to submersion in salt or fresh water to surfaces which are constantly exposed to a saltwater or freshwater environment to prevent the growth of microbial films, simple and complex plants, or the attachment of marine or fresh water animals on these surfaces. A specific formulation is 83% bioadhesive polyphenolic protein and 17% (w/w) mussel adjuvant protein dried and treated for 20 min. with 600 Units/mg mushroom tyrosinase. Oxidation of available L-dopa residues to a quinone mimics the phenomenon found in nature known as "quinone tanning", known to produce water-resistant, enzyme resistant, fouling resistant structures.

(9) An anti-corrosion and scale-inhibiting, water-impervious coating which may be applied under water or prior to submersion in salt or fresh water to metal and other surfaces constantly exposed to saltwater and freshwater environments to prevent corrosion, scaling, and degradation of these surfaces. A specific formulation for this application is as described in (8) with up to 10 repeated coatings of protein layers followed by oxidation.

(10) An adhesive to bond plant and tree grafts together while promoting hybrid development and genetic changes in plant materials, or for the purpose of plant repair or reconstruction following injury, and as a would closure material for repair of injury or disease. A specific formulation for this application is as described in (6).

(11) A nonbiodegradable, nontoxic adhesive coating to be applied to plant surfaces as an antifouling agent against blight and other fungal diseases. A specific formulation for this application is as described in (8).

(12) A conductive adhesive which may be used to join two substrates through which an electrical current will be passed without inducing excessive resistance. A specific formulation for this application comprises 65% (w/w) bioadhesive polyphenolic protein; 34% (w/w) collagen slurry; 1% (w/w) ferrocene as the conductive additive; and 6,000 Units/mg protein of mushroom tyrosinase as the cross-linker.

(13) A filter coating agent which may be used as an additive to a nitrocellulose filter or resin beads as used in column chromatography support matrices which would trap heavy metal and other contaminants from fluid, allowing the concentration of those metals or other contaminants to be determined or simply recovered with high efficiency. A useful formulation is 50% (w/w) bioadhesive polyphenolic protein with an appropriate amount of a cross-linker, and 50% (w/w) collagen. Another useful formulation is synthetic peptide with the sequence [ala-lys-pro-ser-tyr-hypro-hypro-thr-tyr-lys], repeated 10 times with 18,000 Units/mg mushroom tyrosinase.

(14) A medical adhesive which may be used to implant drugs, hormones, biological factors, medications, physiologic and/or metabolic monitoring devices, antibiotics, single cells, sheets of cells, and the like in intact tissues and/or at the sites of surgical and medical therapeutic or reparative procedures through the attachment of such agents directly to the adhesive polymer or the attachment of capsules containing such agents as prophylaxis or as follow-up to medical procedures in order to promote healing or re-establish specific metabolic functions, e.g., skin grafting, implantation of insulin-producing cells (Islets of Langerhans). A useful formulation is as described in (6).

(15) A primer which may be used for the treatment of surfaces prior to the application of a paint or adhesive which would reduce the need for meticulous cleaning of surfaces by excluding water, penetrating oxide layers and/or inhibiting metallic oxide to hydroxide conversion, penetrating organic debris layers, or penetrating microbial film layers. These surfaces would include metals, wood, plastics, silicates (cement, glass), soft and hard tissues (bones, teeth). Two useful formulations are: (a) synthetic peptide having the sequence [ala-lys-pro-ser-tyr-hypro-hypro-thr-tyr-lys]repeated 10 times with 18,000 Units/mg mushroom tyrosinase; and (b) 50% (w/w) bioadhesive polyphenolic protein with appropriate amount of cross-linker and 50% (w/w) collagen.

(16) An additive which may be used with any other adhesive formulation that would impart the specific properties herein described to another adhesive. These properties include: compatibility with hygrocopic, saline substrates in and around living tissues, marine environments, and the moist environments of fresh waters: the ability to impart anti-corrosion, anti-scaling, and/or anti-fouling properties to the resulting composition; the ability to complex with metals, ions, other polyamines, and biological substances. A useful formulation is synthetic peptide having the sequence [ala-lys-pro-ser-tyr-hypro-hypro-thr-tyr-lys]repeated 10 times, with 18,000 Units/mg mushroom tyrosinase, incubated together for 5 minutes at room temperature before addition to another adhesive system at a ratio of 1:10 (w/w).

The following specific examples are here given to illustrate further the various uses of the adhesive compositions of this invention. They are included here for illustrative purposes only and are not to be construed as limitations on the invention herein claimed. As one skilled in the art understands, many variations and modifications may be made to the invention herein described which fall within the spirit and scope of this invention.

EXAMPLES 1-3

To demonstrate the adhesive function of bioadhesive formulations, two 1-cm wide strips of aluminum foil were bonded together in a lap shear test using the following formulation: 74% bioadhesive polyphenolic protein (4.3 mg/ml in water); 26% (w/w) collagen slurry as a filler (25% w/w collagen in pH 6.5, 0.1 M phosphate buffer); 18,600 Units/mg mushroom tyrosinase cross-linker (216 Units/$\mu$l in pH 6.5, 0.1 M phosphate buffer). The above formulation was applied evenly with a syringe over a 1 square centimeter section at the end of each aluminum foil strip, and the two coated sections then joined so that the bonded area of overlap was 1 cm$^2$. The bond was allowed to set 2.5 hours at room temperture (21° C.), and was then tested and found to provide a shear strength of 320 gm/cm$^2$.

In a second example, two 1-cm strips of aluminum foil were bonded together with the bioadhesive formulation described above so that the area of overlap was 1 square centimeter. The sample was allowed to cure 24 hours at room temperature (21° C.) and the measured shear strength was in excess of 916 gm/cm$^2$.

In a third example, aluminum foil samples prepared as above using the bioadhesive formulation were kept under water for a 1-hour setting period. The bioadhesive polyphenolic protein formulation was found to provide a shear strength at least fivefold greater than that achieved with a cyanoacrylate control.

EXAMPLES 4-7

To establish the biomedical applications of the bioadhesive formulation, a formulation was prepared as follows: 65% (w/w) bioadhesive polyphenolic protein (5.5 mg/ml in water); 35% (w/w) collagen slurry as a filler (25% w/w in pH 7, 0.1 M phosphate buffer); 6000 Units/mg mushroom tyrosinase cross-linker (216 Units/ul in pH 7, 0.1 M phosphate buffer). A bovine meniscus which had been surgically severed longitudinally was subsequently bonded together with the above formulation applied evenly with a syringe over the two cut surfaces of about 4 square centimeters each. The bond was allowed to set 1 hour at 37° C., and was then tested and found to provide a tensile strength of 85 gm total, or 21.2 gm/cm$^2$.

Canine meniscus was bonded with a second bioadhesive formulation. The formulation contained 65% (w/w) bioadhesive polyphenolic protein (5.5 mg/ml in water); 35 % (w/w) collagen slurry (25% w/w in pH 7, 0.1 M phosphate buffer); 12,600 Units/mg mushroom tyrosinase cross-linker (216 Units/$\mu$l in pH 7, 0.1 M phosphate buffer). The meniscus, which had been surgically severed longitudinally, was subsequently bonded together with the formulation applied evenly with a syringe over the two (1.5 cm$^2$ each) cut surfaces. The bond was allowed to set 30 minutes at 37° C., and was then tested and found to provide a tensile strength of 13 gm total, or 8.7 gm/cm$^2$ In yet another example, spinal vertebrae were used as a model for bone-to-bone repair. The bioadhesive formulation employed contained 59% (w/w) bioadhesive polyphenolic protein (4.3 mg/ml in water); 41% collagen slurry (25% w/w in pH 7, 0.1 M phosphate buffer); 14,800 Units/mg mushroom tyrosinase cross-linker (216 Units/$\mu$l in pH 7, 0.1 M phosphate buffer). Two spinal vertebrae were bonded together with the formulation applied evenly with a syringe over the two (0.5 cm$^2$ each) opposing surfaces The bond was allowed to set 43 minutes at 37° C., and was then tested and found to provide a tensile strength of 38 gm total, or 76 gm/cm$^2$.

The preceding example with spinal vertebrae was repeated with an adhesive formulation containing different ratios of the same components, namely, 74% (w/w) bioadhesive polyphenolic protein (4.3 mg/ml in water); 26% (w/w) collagen slurry (25% w/w in pH 7,. 0.1 M phosphate buffer); 18,400 Units/mg mushroom tyrosinase cross-linker (216 Units/$\mu$l in pH 7, 0.1 M phosphate buffer). Two spinal vertebrae were bonded together with the formulation applied evenly with a syringe over the two (0.5 cm$^2$ each) opposing surfaces. The bond was allowed to set 47 minutes at 37° C., and was then tested and found to provide a tensile strength of 44 gm total, or 88 gm/cm$^2$.

EXAMPLE 8

Examples 8 and 9 demonstrate the advantages of pre-treating tissues with the bioadhesive polyphenolic protein prior to bonding Two 1-cm wide strips of calf stomach with a tissue thickness of approximately 1.5 mm were bonded together end-to-end using the following procedure. First, the tissue was primed by applying 50 $\mu$l of solution to the two surfaces (50% (w/w) bioadhesive polyphenolic protein, 50% (w/w) collagen). The surfaces were allowed to set briefly and cyanoacrylate adhesive was applied and allowed to set for 51 minute at 37° C. The measured tensile strength of the bond was found to be 1,230 gm/cm$^2$.

EXAMPLE 9 FOR COMPARISON

In a control experiment relating to the above Example 8, two 1-cm-wide strips of calf stomach with a tissue thickness of 1.5 mm were bonded together end-to-end using cyanoacrylate. The bond was allowed to set for 51 min. at 37° C., and was then tested and found to provide a tensile strength of 85 gm, or 570 gm/cm$^2$.

EXAMPLE 10

Antifeuling applications were illustrated using a cellulose paper substrate coated with different preparations of bioadhesive polyphenolic protein with and without oxidation with mushroom tyrosinase. The oxidation of L-dopa to the quinone produces what in nature is referred to as quinone-tanned structures. Two examples of quinone tanning which achieves environmental stability are the tanning of hides in leather processing and the brown, rigid skate egg cases. Cellulose strips (7.5 cm×2.5 cm) were treated in the following manner: (1) two strips were soaked and dried 9 times in a solution containing bioadhesive polyphenolic protein at 2.9 mg/ml in 5% v/v acetic acid; (2) two strips soaked and dried 9 times in bioadhesive polyphenolic protein preparation in (1), with each drying followed by a 10-minute incubation in mushroom tyrosinase (43 Units/$\mu$l in phosphate buffer, 0.1 M, pH 7.0) (3) two strips soaked and dried 9 times in bioadhesive polyphenolic protein preparation at 2.9 mg/ml mixed 50:50 with an adjuvant L-dopa-containing protein at 2.14 mg/ml in sodium acetate (0.1 M, pH 5.0) followed by enzyme oxidation as in (2); (4) two strips as untreated cellulose controls. These strips were then suspended in a saltwater aquarium and observed for one week. Both the cellulose controls and the unoxidized bioadhesive polyphenolic protein showed marked signs of decomposition and microbial growth in four days, while both oxidized preparations were intact after seven days.

EXAMPLE 11
Isolation and Purification via Extraction of Bioadhesive Polyphenolic Protein 300 grams of marine mussel, *M. Edulis,* feet are combined with 900 mls of neutral salt buffer which contains 1M sodium chloride, 0.05M tris (hydroxymethyl) aminomethane (pH 7.5), 1 mM phenylmethylsulfonylfluoride, 10mM N-ethylmaleimide, 0.025 M ethylenediamine tetraacetic acid and 1 mM potassium cyanide plus 9 mls of antifoam concentrate in a commercial blender on high speed and thoroughly blended, precipitating the bioadhesive polyphenolic protein. The mixture is centrifuged at 10 K rpm for 15 minutes. The pellet is resuspended in 900 mls of 5% acetic acid using the blender on high speed. Bioadhesive polyphenolic protein remains in the supernatant during centrifugation at 10 K rpm for 45 minutes. The approximately 1000 mls of supernatant is put into an ice bath with continual stirring. 5 mls of 2M sodium borate plus 95 mls of 5 M sodium chloride are added to the stirring supernatant. This mixture is centrifuged at 10K rpm for 15 minutes. The new supernatant is treated identically as above with the addition of four times as much 2M sodium borate and 5 M sodium chloride. Once again, the mixture is centrifuged at 10K for 15 minutes. The pellet is resuspended in the following mixture: 7.5 mls of 2M sodium borate, 50 mls of 5M sodium chloride, 50 mls of distilled water, 37.5 mls of 8M urea in 5% acetic acid, and 5.6 mls of concentrated acetic acid. The mixture is slowly stirred for approximately 16 hours. The suspension is centrifuged at 10 K rpm for 15 minutes. The supernatant is saved and dialyzed (1812K molecular weight cut-off membranes) against 5% acetic acid for approximately 16 hours. Amino acid analysis establishes that the extract contains 45% pure bioadhesive polyphenolic protein. The purity of the extract is governed by the number of extractions effected. The yield of pure bioadhesive polyphenolic protein decreases as the number of extractions increases. All procedures described herein were conducted at 4° C.

Further chromatographic purification

Using liquid chromatography, SE Sephadex resins retain polyphenolic proteins in 5.5% Guanidine hydrochloride (GuHCl) in 5% acetic acid. The protein is then eluted from the resin with a gradient of 5.5–20% GuHCl in acetic acid, the peak areas pooled and dialyzed against 5% acetic acid to remove the GuHCl. Storage of the proteins is most stable at 4° C. in 5% acetic acid. Prior to its use as an adhesive, in vivo or in contact with live cells, bioadhesive polyphenolic proteins must be dialyzed against water to raise the pH of the solution to near neutrality and the preparation must be concentrated to between 3 and 10 mg/ml. This is accomplished using an ultrafiltration membrane with pore size exclusion limits of 30,000 or less. This is not necessary when bioadhesive polyphenolic proteins are dried onto an inert substrate prior to use.

EXAMPLE 12

This example demonstrates that pure bioadhesive polyphenolic protein alone does not impart maximal adhesive strength for bonding without the presence of additional cross-linking agents and fillers.

(I). A constant amount of protein, either 95% pure bioadhesive polyphenolic protein alone, boiled casein alone, or a combination of bioadhesive polyphenolic protein and casein were applied to strips of aluminum foil and tested for bond strength. Total protein per bond area was kept at 20 $\mu$grams of protein delivered in 4 $\mu$l of 5% acetic acid and was applied to a bond area of 1.3 cm$^2$. The formulation of proteins applied to the bonds were: 20 $\mu$grams of bioadhesive polyphenolic protein alone, 20 $\mu$grams of boiled casein alone, and a mixture of 10 $\mu$grams of bioadhesive polyphenolic protein plus 10 $\mu$grams of boiled casein. Bonds were allowed to cure for one hour, then measured by clamping the strips between a pressure guage (0–500 or 0–5000 Gm range) and a geared motor with a piston producing strain at a rate of 25 grams per second. All procedures were performed at room temperature. The data are the average of five assays per formulation. For casein alone, 275; for pure bioadhesive polyphenolic protein alone, 214; and for the combination of the two, 1026 gm/1.3 cm$^2$. The data indicates that enhanced results can be obtained when a filler is admixed with the bioadhesive 28 polyphenolic protein, as indicated by the increase in strength of the mixtures' bond by a factor of 2 greater than the sum of the two proteins used alone.

(II.) In order to demonstrate the effect of a cross-linking agent on the bioadhesive polyphenolic protein formulation, a cross-linking agent, 3,3'-dithiobis(sulfosuccinimidylproprionate) (DTSSP), was incorporated into the formulation at varying concentrations and compared to a control having no cross-linking agent. DTSSP is a water soluble cross-linker of lysines with optimum activity at pH = 7. Both bioadhesive polyphenolic protein and casein were prepared at 10 mg/ml in distilled water (pH = 6) and in 0.1 M phosphate buffer (pH = 7). DTSSP was prepared in 0.1 M phosphate buffer (pH = 7) at a concentration of 400 $\mu$M. Mixtures were placed on foil and measured as described above, with each number representing the average of five trials.

| $\mu$g bioadhesive polyphenolic protein | $\mu$g casein | DTSSP (mM final concentration (wt. %) | | shear strength (gm/cm$^2$ × 1.3) |
|---|---|---|---|---|
| 0.1M Phosphate Buffer pH 7 | | | | |
| 10 | 10 | 0 | (0.0%) | 250 |
| 10 | 10 | 100 | (1.4%) | 1310 |
| 10 | 10 | 50 | (0.7%) | 1560 |

| μg bioadhesive polyphenolic protein | μg casein | DTSSP (mM final concentration (wt. %) | | shear strength (gm/cm² × 1.3) |
|---|---|---|---|---|
| | | Distilled H₂O | | |
| 10 | 10 | 0 | (0.0%) | 775 |
| 10 | 10 | 50 | (0.7%) | 1690 |

The data show that an increase in pH to accommodate the cross-linker DTSPP decreases the strength of bioadhesive polyphenolic protein plus casein formulation to 250 and 775 (compared to 1026 gm/1.3 cm² in acid pH). In both cases, it can readily be seen that DTSSP significantly enhances bond strength.

EXAMPLE 13

In this example, bovine corneas were used to demonstrate that while pure bioadhesive polyphenolic protein does have some adhesivity, this adhesivity can be greatly enhanced by the addition of, in this example, a cross-linking agent. Bovine corneas were removed from ennucleated eyes and scraped with a scalpel for removal of endothelial and epithelial cells. Tissue strips (2×1 cm²) were prepared and anterior to posterior bonds (1 cm² in area) were tested. Pure bioadhesive polyphenolic protein (3.2 μg/μl in water) was applied with a microliter pipet to both bond sides, 8.1 μl per side, and spread over the 1 cm² area. The two tissues were immediately joined, and incubated for 20 minutes at room temperature with gentle (5 gm) pressure under conditions which keep the tissue moist. The tissues were clamped, suspended vertically and small weights added at a rate of about 3 gm per second. Bioadhesive polyphenolic protein alone with a total of 51.8 μg/cm² tissue yielded a strength of 7 gm/cm². The same amount of protein, 51.8 μg with added catechol oxidase cross-linking agent at 11.76 U/μg bond protein yielded a strength of 68 gm/cm 2.

Bond strength was further enhanced with careful removal of debris from the corneal surface with a phosphate-buffered saline rinse (pH7-7.5). The formulation: 9 μl of a mixture of pure bioadhesive polyphenolic protein (21 μl of 5 μg/μl) plus catechol oxidase (1.16 μl of 325 U/μl) yields 128 gm/cm². Repeating the test set forth hereinabove, bond strength typically ranging from about 150-200 gm/cm². are obtained.

EXAMPLE 14

This example demonstrates the use of bioadhesive polyphenolic protein for sealing ophthalmic perforations using alloplastic materials. Bovine corneas and HYPAN discs (HYPAN is a trademark of Kingston Technologies, Dayton, New Jersey) were employed. HYPAN discs are useful for this application because they are manufactured from gas permeable polyacrylonitrile block copolymer hydrogels containing 90% water.

Epothelial cells are scraped off over a region about 15-20 mm in diameter on the bovine cornea using a scalpel. A perforation is prepared by jabbing in the center of the scraped corneal area with a scalpel. An 18 gauge needle is inserted into the anterior chamber by puncturing the cornea near the corneal/scleral junction and checked for fluid path continuity by pressurizing the anterior chamber using manual pressure and looking for fluid leakage through the needle. The scraped area is then rinsed with deionized water. Excess water is then blown off.

10 μl of chromatographically purified bioadhesive polyphenolic protein (5.8 mg/ml in H₂O) and 0.94 μl of catechol oxidase (648μg/μl in 0.1M phosphate buffer) are mixed and applied in the immediate area of the perforation. A HYPAN disk is applied and smoothed out over the cornea insuring no folds in the cornea are present under the disc. A dialysis bag is applied over the joint and the joint is allowed to cure for the time periods ranging from 5 to 20 minutes. A manometer is attached to the needle and the dialysis bag is removed.

The eye is pressurized to about 120"/min, while monitoring leakage and pressure. The pressure recorded is the reading attained at the first sign of leakage. The pressure sustained equals the net height of the water in the manometer (65"-1"- reading). The pressure is converted to mm Hg by dividing by 0.535. The data is the average of seven assays wherein the cure time ranges from five to twenty minutes. The average mm of mercury sustained was greater than 93. The results show that bioadhesive polyphenolic protein is an excellent adhesive for sealing ophthalmic incisions and perforations using an alloplastic material.

EXAMPLE 15

In this example, Hypan ® polyacrylonitrile was used to demonstrate that decapeptide oligomers alone are not suitable for use as adhesives because cross-linking thereof will not result in a polymer of sufficient molecular weight to exhibit adhesivity or produce a polymer with sufficient available reactive groups for further interaction as compared to the natural bioadhesive polyphenolic protein, for example. Hypan ® hydrogel contains at least 80% water.

The Hypan ®-Hypan ® hydrogel bond was tested for its resistance to an acid bath (0.5M HCl) as a means of indicating the adhesive characteristics of each material. The acid test is used as an indicator of bond strength (cohesive), speeding up the separation of the Hypan ® hydrogel strips for more rapid analysis. L Hypan ® hydrogel strips bonded with uncross-linked natural bioadhesive will separate in water within two hours, but will separate in less than 1 minute in the acid. The bond formed by cross-linked polyphenolic protein will remain intact in water or acid for at least a week.

Hypan ® hydrogel was cut into strips 1 ×2 cm and soaked in phosphate buffered saline pH 7.0 (PBS) prior to use. Glutaraldehyde (25% in H₂O) was employed as the cross-linking agent.

10 μg of the decapeptide and the bioadhesive polyphenolic protein were each placed directly on separate pieces of Hypan ® hydrogel with 2 μl of 0.2M sodium acetate, pH-7.0. One μl of glutaraldehyde (25% in H₂O) was then added to each and each was mixed, spread over a 1 cm ²area. A second strip was immediately placed directly on top of the treated strip. The overlapped strips were allowed to incubate for 3 minutes and then the bond strength was tested. The bonded hydrogel was was then placed in an acid bath for 15 minutes prior to repeated testing of the bond strength. As controls, the same procedure was followed using water instead of glutaraldehyde.

Natural bioadhesive polyphenolic protein effected bonding of Hypan ® hydrogel strips in the uncrosslinked and cross-linked states. Only the cross-linked natural bioadhesive polyphenolic protein held together in acid. The decapeptide, with or without cross-linking agent, showed no adhesive properties as the Hypan ® hydrogel strips slid apart without resistance prior to acid treatment.

Accordingly, glutaraldehyde can be used as a cross-linking agent in the present invention if the starting material (adhesive) is of a molecular weight sufficient to produce a cross-linked product to a sufficient molecular weight to exhibit adhesivity.

EXAMPLE 16

This example demonstrates the use of bioadhesive polyphenolic protein for bone-to-bone repair. The knee joint of a horse was used to evaluate bonding. The bioadhesive formulation employed contained 14 μl of bioadhesive polyphenolic protein (5 mg/ml in water) and 2 μl of a 30 mM aqueous solution of Bis(sulfosuccinimidyl) suberate per $cm^2$ area.

Pieces of bone were chipped off the knee joint and were bonded back in their original location with the aforementioned formulation. Both surfaces of the bond area were rinsed with water and dried with gauze. The surfaces were then cleansed with a solution of the bioadhesive polyphenolic protein (5 mg/ml in water) by applying the solution and allowing it to sit for about 30 to 60 seconds but not allowing the solution to dry. The surface was then rinsed with water and the area dried with gauze. The cleaning step is optional, although preferred as it is believed that the bioadhesive polyphenolic protein binds to loose debris which is then removed by rinsing with water.

14 μl of the aforementioned formulation was then applied to each surface (14 μl/$cm^2$ of bone). The bone chip was then pressed back into its original space and held for 5 minutes. The bones were then allowed to set for an additional 30 minutes prior to testing the shear strength of the bond.

The strength of the bond is evaluated by applying a direct shear force to the bone chip. The bone chips did not move at all after submission to the direct shear force.

EXAMPLE 17

This example demonstrates the use of bioadhesive polyphenolic protein for skin grafting applications. Porcine skin was used to evaluate bonding.

Frozen, defatted porcine skin was cut into 2 × 1 cm strips, covered with wet gauze and refrigerated to allow for complete thawing and hydration to occur. After approximately two hours, the dermal side of the porcine strips are swabbed with ethanol and dried with gauze. The bioadhesive formulation contains 14 μl of pure bioadhesive polyphenolic protein (5 mg/ml in water); 4 μl of buffer (specified in Table I) and 2 μl of a 30 mM (17.18 mg/ml) aqueous solution of Bis(sulfosuccinimidyl) suberate. The bioadhesive formulation is mixed on a clean polystyrene dish in the order set forth. 14 μl of the bioadhesive formulation is applied to the bond site (1 cm $^2$) on one porcine strip. A second ethanol treated prepared porcine strip is overlapped at the bond site and a plastic dish containing a 295 g weight placed thereon for a period of 10 minutes.

The shear strength of the bond is then tested by vertically hanging the bonded tissue and adding weights to the bottom until the bond breaks. The results employing various buffer solutions are set forth in Table I.

TABLE I

| Buffer | pH | Average shear Strength |
|---|---|---|
| 0.05 M phosphate buffer | 7 | 158 g/$cm^2$ |
| 0.025 M phosphate buffer | 7 | 132 g/$cm^2$ |
| 0.1 M Bicarbonate/carbonate buffer | 9.2 | 147 g/$cm^2$ |

EXAMPLE 18

In this example, bovine corneas were used to establish the optimum ratio at which pure bioadhesive polyphenolic protein, cross-linking agent and buffer will produce an effective formulation for bonding corneal tissues together. Bovine corneas were removed from ennucleated eyes and sliced into strips (2×1 $cm^2$). The strips of bovine corneas were then washed with 100 μl of phosphate buffered saline solution and immediately dried. Anterior to posterior bonds (1 $cm^2$ in area) were tested.

On a separate clean surface, 21 μl of pure bioadhesive polyphenolic protein (5 mg/ml$H_2O$), 5 μl of 0.25 M $PO_4$ buffer and 1.16 μl of Bis(sulfosuccinimidyl) suberate ($BS_3$) at a 15 mM concentration in water are mixed together. The formulation was then applied to one strip of bovine cornea and spread over a surface area of approximately 1 $cm^2$. The exact amount of the bioadhesive formulation and the area covered are set forth in Table 2. A second strip of bovine cornea was then gently laid on top of the first covering only the same 1 $cm^2$ area.

The bond was then weighted down with a small water bag containing approximately 15 ml of water and the bond was allowed to set for 20 minutes. The shear strength of the bond was then tested.

One end of the bonded cornea strips was clipped to a ring stand and a water bag was clipped to the opposite end. Water was allowed to flow into the bag at a constant rate of 200 ml/minute until a separation of the bonded area occurred. The weight of water was measured and converted to a shear strength measurement. The results are set forth in Table 3.

TABLE 3

| μl of formulation | Surface area covered | Water weight (gm) | Shear strength (g/$cm^2$) |
|---|---|---|---|
| 8 | 0.64 | 245 | 383 |
| 11 | 0.75 | 305 | 407 |
| 12 | 0.64 | 285 | 445 |
| 8 | 0.64 | 400 | 625 |

The experimental results establish that at the foregoing concentrations, the formulation containing bioadhesive polyphenolic protein and cross-linking agent produce a bond exhibiting a shear strength greater than 100 g/cm $^2$ on soft tissue. Since the tissue is not, of course, homogeneous, the numerical values obtained are not reproducible in the sense of exact values but, the results are consistent as to the requirement of a shear strength of at least 100 g/$cm^2$ on soft tissue.

What is claimed is:

1. A water-imperious adhesive or coating formulation exhibiting an adhesive strength of at least about 100 gm/$cm^2$ when used on soft tissue comprising:
   (1) a bioadhesive polyphenolic protein component having from about 5 to about 99 weight percent of a proteinaceous substance comprising from about 50 to about 150 of the following repeating decapeptide unit:

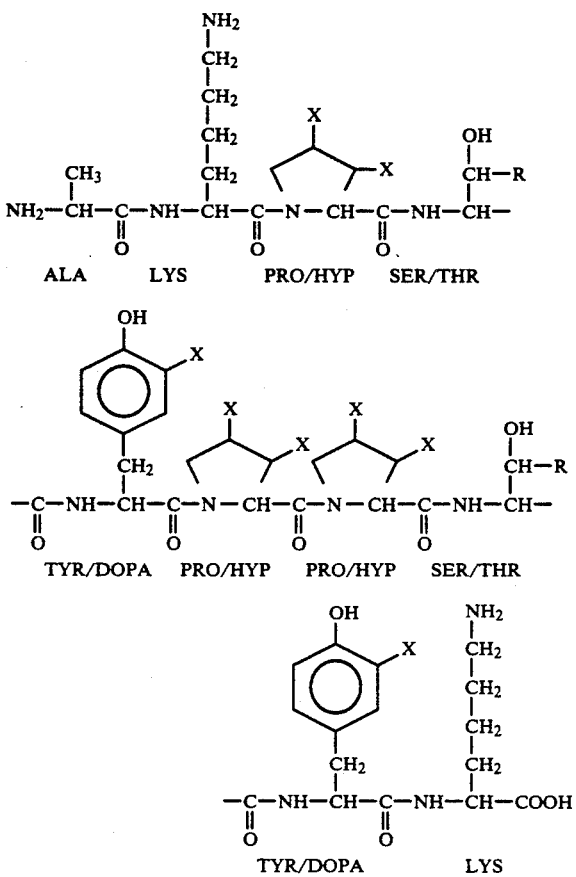

in which each X is hydrogen or hydroxyl, and each R is hydrogen or methyl;
(2) from about 1.0 to about 40 weight percent of a cross-linking agent which promotes cross-linking of the decapeptide;
(3) one or more additives which promote the desired properties of the formulation, said additives comprising at least one surfactant and being present in an amount of from 0% to about 90% by weight, and
(4) a filler compatible with the intended use of the formulation, said filler being present in an amount of from 0% to about 50% by weight,
wherein the bioadhesive polyphenolic protein component (1) is derived from the marine mussel.

2. A water-impervious coating formulation according to claim 1 wherein said proteinaceous substance comprises from about 50 to about 150 of said decapeptide unit.

3. A water-impervious adhesive according to claim 1 wherein said adhesive strength is at least about 150 gm/cm$^2$.

4. A water-impervious adhesive or coating formulation according to claim 1 in which the bioadhesive polyphenolic protein component and the cross-linking agent together are present in an amount ranging from about 25 to about 90 weight percent of the formulation.

5. A water-impervious coating formulation according to claim 2 for use in an underwater environment in which: (a) the bioadhesive polyphenolic protein component and the cross-linking agent are together present in an amount ranging from about 50 to about 80 weight percent; and (b) a surfactant functioning as a spreading agent in an amount ranging from about 20 to about 40 weight percent of the formulation.

6. A water-impervious formulation according to claim 5 in which the surfactant is sodium dodecylsulfate or sodium dodecylbenzenesulfonate.

7. A water-impervious adhesive formulation according to claim 1 for biomedical use in which each additive and filler is compatible with the organs to which the formulation is applied.

8. A biomedical adhesive formulation according to claim 7 for use in orthopedic repair, reconstruction or prosthetics, in which; (a) the bioadhesive polyphenolic component and the cross-linking agent are together present in an amount ranging from about 30 to about 70 weight percent; (b) the filler is present in an amount ranging from about 30 to about 60 weight percent.

9. A biomedical adhesive formulation according to claim 8 in which the filler is selected from the group consisting of collagen, hyaluronic acid, chondroitan sulfate, elastin, laminin, casein, hydroxyapatite, or a similar naturally occurring proteinaceous, inorganic, or mucopolysaccharide substance.

10. A biomedical adhesive formulation according to claim 9 in which the filler is collagen.

11. A biomedical adhesive formulation according to claim 9 in which the cross-linking agent is mushroom tyrosinase.

12. An adhesive formulation according to claim 1 for use in ophthalmic surgery in which the bioadhesive polyphenolic protein component and the cross-linking agent are together present in an amount varying from about 70 to about 100 weight percent.

13. An adhesive formulation according to claim 12 in which the cross-linking agent is mushroom tyrosinase.

14. An adhesive formulation according to claim 12 for sealing ophthalmic incisions and perforations with alloplastic materials in which the bioadhesive polyphenolic protein component and the cross-linking agent are together present in an amount varying from about 3 to about 100 weight percent and a collagen filler is incorporated in amounts ranging from 0 to about 40 weight percent.

15. An adhesive and coating formulation according to claim 1 for bonding plant materials or coating plant surfaces in which each additive and filler is biochemically compatible with the plant to which the formulation is applied.

16. An adhesive formulation according to claim 1 for joining substrates through which an electric current is to be passed, said formulation additionally containing electrically conductive additives in an amount ranging from about 10 to about 80 weight percent.

17. A method for adhering two or more substrates in an underwater environment which comprises applying to the adherent surfaces either under water or prior to submersion in water an adhesive formulation according to claim 1.

18. A method for coating an underwater surface so as to prevent the growth of microbes or plants thereon, or the attachment thereto of marine animals, said method comprising applying to said surface a formulation according to claim 5.

19. A method for preventing corrosion of an underwater surface which comprises applying to said surface a coating formulation according to claim 5.

20. A method of priming a surface for subsequent application of a coating or adhesive which method comprises applying to said surface a formulation according to claim 1.

21. In orthopedic repair and reconstruction, a method for adhering bone, tendon, ligament, meniscus, muscle, each to each other or adhering any of them to alloplastic materials, which method comprises applying to a surface on which adhesion is sought a formulation according to claim 8.

22. A method according to claim 21 in which, in the formulation, the biocompatible filler is collagen.

23. A method according to claim 21 in which, in the formulation, the cross-linking agent is mushroom tyrosinase.

24. In dentistry, a method for adhering retainers, bridges, crowns or filler material to tooth structure, for securing loose teeth and for repairing broken teeth, which method comprises applying to the surface on which adhesion or repair is sought a formulation according to claim 7.

25. A method for attaching donor tissue or alloplastic grafts to promote wound and incision closure and prevent bacterial contamination in soft tissue which comprises applying to the surface to be treated a formulation according to claim 7 and attaching said donor tissue or alloplastic graft thereto.

26. A method for sealing wound or incision closures and the regions adjacent thereto which have been punctured by associated surgical closure devices to substantially reduce fluid seepage therethrough which comprises applying to the site to be sealed a formulation according to claim 7.

27. A method for treating wounds, fractures and dislocations in animals which comprises applying to the surface to be treated a formulation according to claim 7.

28. A method for implanting in a patient a prosthesis or medical device containing drugs, medications, single cells or sheets of cells, or electronic circuitry, which comprises adhering said prosthesis or device to the desired site in the patient with an adhesive formulation according to claim 7.

29. In ophthalmic surgery, a method for repair or attachment of alloplastic or donor tissue which comprises applying to the surfaces to be adhered an adhesive formulation according to claim 12 and attaching said alloplastic or donor tissue thereon.

30. A method for sealing ophthalmic incisions or punctures with alloplastic material which comprises applying to the surface to be treated a formulation according to claim 12 and attaching said alloplastic material thereto.

31. A method for treating plants for the purpose of repairing injury, reconstruction, wound closure, grafting or promoting hybridization or genetic alteration, which comprises applying to surfaces which are to be adhered a formulation according to claim 15.

32. A method for protecting plants against attack from fungal diseases which comprises applying to the surface areas of the plant subject to fungal attack a coating formulation according to claim 15.

33. A method for joining two substrates through which an electric current is to be passed which comprises adhering the substrates to each other with an adhesive formulation according to claim 16.

34. A method for separating heavy metals and contaminants from fluids which comprises applying to a nitrocellulose filter or to resin beads used as support matrices in ultrafiltration procedures and column chromatography, respectively, a coating formulation according to claim 1.

* * * * *